US011481985B1

(12) United States Patent
Sivaswamy et al.

(10) Patent No.: US 11,481,985 B1
(45) Date of Patent: Oct. 25, 2022

(54) AUGMENTED REALITY ENABLED APPETITE ENHANCEMENT

(71) Applicant: INTERNATIONAL BUSINESS MACHINES CORPORATION, Armonk, NY (US)

(72) Inventors: Hemant Kumar Sivaswamy, Pune (IN); Shikhar Kwatra, San Jose, CA (US); Tanvi Tayal, White Plains, NY (US); Venkata Vara Prasad Karri, Visakhapatnam (IN)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 0 days.

(21) Appl. No.: 17/238,262

(22) Filed: Apr. 23, 2021

(51) Int. Cl.
*G06T 19/00* (2011.01)
*G06N 20/00* (2019.01)
*G16H 20/60* (2018.01)

(52) U.S. Cl.
CPC .......... *G06T 19/006* (2013.01); *G06N 20/00* (2019.01); *G16H 20/60* (2018.01)

(58) Field of Classification Search
None
See application file for complete search history.

(56) References Cited

U.S. PATENT DOCUMENTS

| 10,790,054 | B1* | 9/2020 | Vleugels | G16H 20/60 |
| 11,127,066 | B2* | 9/2021 | Wang | G06F 16/24578 |
| 2001/0021694 | A1 | 9/2001 | Portman | |
| 2015/0332620 | A1* | 11/2015 | Sako | G06K 9/00671 345/8 |
| 2016/0170998 | A1* | 6/2016 | Frank | G06F 16/337 707/748 |
| 2016/0171514 | A1* | 6/2016 | Frank | G06Q 30/02 705/7.29 |
| 2016/0189057 | A1* | 6/2016 | Rao | G06N 20/00 706/12 |
| 2016/0224803 | A1* | 8/2016 | Frank | G06F 21/6245 |

(Continued)

FOREIGN PATENT DOCUMENTS

| CA | 2534530 C | 3/2005 |
| CN | 101247734 B | 8/2008 |

OTHER PUBLICATIONS

Alzheimer's Society, "Poor Appetite and Dementia", https://www.alzheimers.org.uk/get-support/daily-living/poor-appetite-d..., accessed Feb. 8, 2021, pp. 1-7.

(Continued)

*Primary Examiner* — Michael J Cobb
(74) *Attorney, Agent, or Firm* — Andre L. Adkins

(57) ABSTRACT

The exemplary embodiments disclose a method, a computer program product, and a computer system for enhancing a user's appetite with one or more augmented reality devices. The exemplary embodiments may include collecting data of the user, the user's environment, and one or more consumable items, extracting one or more features from the collected data, determining one or more augmented reality appetite enhancements based on the extracted one or more (Continued)

features and one or more models, and enhancing the user's appetite by way of the one or more augmented reality devices according to the determined one or more augmented reality appetite enhancements.

17 Claims, 6 Drawing Sheets

(56) References Cited

U.S. PATENT DOCUMENTS

| | | | | |
|---|---|---|---|---|
| 2017/0323481 | A1* | 11/2017 | Tran | H04N 5/23212 |
| 2018/0089739 | A1* | 3/2018 | Cecchi | G06Q 30/0631 |
| 2018/0286351 | A1* | 10/2018 | Fateh | G06Q 30/0641 |
| 2019/0108191 | A1* | 4/2019 | Frank | G06F 16/337 |
| 2019/0160286 | A1 | 5/2019 | Yang | |
| 2019/0252079 | A1* | 8/2019 | Constantin | A61B 5/0024 |
| 2020/0065682 | A1* | 2/2020 | Paulina | G09B 19/00 |
| 2020/0152312 | A1* | 5/2020 | Connor | G06K 9/00335 |
| 2020/0289055 | A1* | 9/2020 | Vleugels | G16H 40/67 |
| 2020/0342979 | A1* | 10/2020 | Sadowsky | A61B 5/165 |
| 2021/0117823 | A1* | 4/2021 | Neumann | G06F 16/285 |
| 2021/0153479 | A1* | 5/2021 | Mindel | G06T 7/0012 |
| 2021/0158918 | A1* | 5/2021 | Neumann | G16H 10/60 |
| 2021/0191986 | A1* | 6/2021 | Okajima | G06F 40/14 |
| 2021/0202067 | A1* | 7/2021 | Williams | G06Q 50/22 |

OTHER PUBLICATIONS

Better Health Channel, "Dementia-eating", https://www.betterhealth.vic.gov.au/health/ConditionsAndTreatments/d . . . , accessed Feb. 8, 2021, pp. 1-5.

Disclosed Anonymously, "Method and System for Controlling an Indoor Ambient Environment for a Patient with Different Light and Sound Needs", IP.com No. IPCOM000236122D, Apr. 7, 2014, pp. 1-4.

https://www.dementiacarecentral.com/caregiverinfo/handsoncare/eating/, "How Dementia Affects One's Ability to Eat and Caregiver Suggestions to Encourage Eating", Oct. 8, 2019, pp. 1-4.

Kerruish, "Arranging sensations: smell and taste in augmented and virtual reality", https://www.tandfonline.com/doi/full/10.1080/17458927.2018.1556952?scroll=top&needAccess=true, Mar. 19, 2019, pp. 1-16.

Mell et al., "The NIST Definition of Cloud Computing", National Institute of Standards and Technology, Special Publication 800-145, Sep. 2011, pp. 1-7.

Sulmont-Rosse et al., "Impact of Olfactory Priming on Food Intake in an Alzheimer's Disease Unit",https://content.iospress.com/articles/journal-of-alzheimers-disease/jad180465 Journal of Alzheimer's Disease, ISSN 1387-2877/18/, 2018, pp. 1-10.

* cited by examiner

AUGMENTED REALITY ENABLED APPETITE ENHANCEMENT

BACKGROUND

The exemplary embodiments relate generally to augmented reality, and more particularly to using augmented reality to enhance a user's appetite.

Many people lose their appetite or suffer from poor appetite for various reasons, including dementia. Those people may be healthier with a better or enhanced appetite. For example, an individual may suffer from dementia and lose their appetite for green leafy vegetables. The individual and the individual's family and friends may wish for the individual to enhance their appetite for green leafy vegetables so that the individual may digest sufficient vitamins and minerals.

SUMMARY

The exemplary embodiments disclose a method, a computer program product, and a computer system for enhancing a user's appetite with one or more augmented reality devices. The exemplary embodiments may include collecting data of the user, the user's environment, and one or more consumable items, extracting one or more features from the collected data, determining one or more augmented reality appetite enhancements based on the extracted one or more features and one or more models, and enhancing the user's appetite by way of the one or more augmented reality devices according to the determined one or more augmented reality appetite enhancements.

BRIEF DESCRIPTION OF THE SEVERAL VIEWS OF THE DRAWINGS

The following detailed description, given by way of example and not intended to limit the exemplary embodiments solely thereto, will best be appreciated in conjunction with the accompanying drawings, in which.

The drawings are not necessarily to scale. The drawings are merely schematic representations, not intended to portray specific parameters of the exemplary embodiments. The drawings are intended to depict only typical exemplary embodiments. In the drawings, like numbering represents like elements.

DETAILED DESCRIPTION OF THE SEVERAL VIEWS OF THE DRAWINGS

Figure 1:
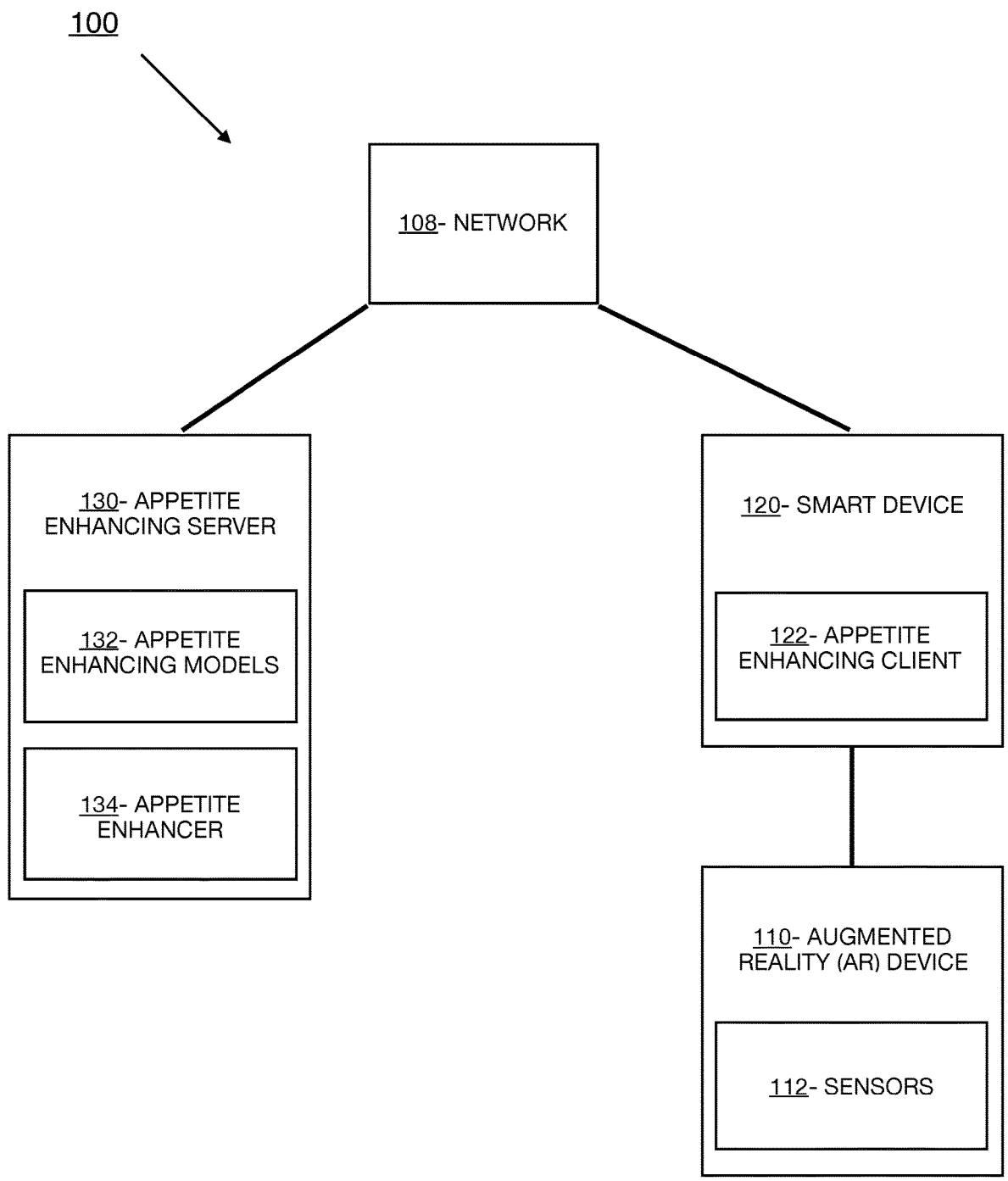
FIG. 1 depicts an exemplary schematic diagram of an appetite enhancing system 100, in accordance with the exemplary embodiments.

Detailed embodiments of the claimed structures and methods are disclosed herein; however, it can be understood that the disclosed embodiments are merely illustrative of the claimed structures and methods that may be embodied in various forms. The exemplary embodiments are only illustrative and may, however, be embodied in many different forms and should not be construed as limited to the exemplary embodiments set forth herein. Rather, these exemplary embodiments are provided so that this disclosure will be thorough and complete, and will fully convey the scope to be covered by the exemplary embodiments to those skilled in the art. In the description, details of well-known features and techniques may be omitted to avoid unnecessarily obscuring the presented embodiments.

References in the specification to "one embodiment," "an embodiment," "an exemplary embodiment," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to implement such feature, structure, or characteristic in connection with other embodiments whether or not explicitly described.

In the interest of not obscuring the presentation of the exemplary embodiments, in the following detailed description, some processing steps or operations that are known in the art may have been combined together for presentation and for illustration purposes and in some instances may have not been described in detail. In other instances, some processing steps or operations that are known in the art may not be described at all. It should be understood that the following description is focused on the distinctive features or elements according to the various exemplary embodiments.

Many people lose their appetite or suffer from poor appetite for various reasons, including dementia. Those people may be healthier with a better or enhanced appetite. For example, an individual may suffer from dementia and lose their appetite for green leafy vegetables. The individual and the individual's family and friends may wish for the individual to enhance their appetite for green leafy vegetables so that the individual may digest sufficient vitamins and minerals.

Exemplary embodiments are directed to a method, computer program product, and computer system for enhancing a user's appetite. In embodiments, machine learning may be used to create models capable of determining one or more appropriate appetite enhancements for a user, while feedback loops may improve upon such models. Moreover, data from user uploads, databases, or the sensors 112 may be used to determine one or more appropriate appetite enhancements for a user. In embodiments, enhancement of appetite may refer to any output of the appetite enhancing system 100 (input to a user) that stimulates one or more of the user's five senses (touch, sight, hearing, smell, and taste), and may be conveyed via audio, video, olfactory, text, touch, etc. A user may wish to enhance their appetite generally or with respect to specific one or more items in a number of circumstances. For example, a user may dislike the taste of spinach, but understand the nutritional value to be gained from consuming spinach. In another example, a user may suffer from an eating disorder and wish to consume a larger quantity of food for health reasons. In another example, a user may suffer from dementia and currently dislike foods that they previously enjoyed consuming. In another example, a child may dislike consuming nutritious foods and benefit from appetite enhancements with respect to the nutritious foods.

In general, it will be appreciated that embodiments described herein may relate to aiding in the enhancement of a user's appetite in general or towards specific consumable items within any environment and for any motivation.

FIG. 1 depicts the appetite enhancing system 100, in accordance with the exemplary embodiments. According to the exemplary embodiments, the appetite enhancing system 100 may include one or more augmented reality (AR) devices 110, one or more smart devices 120, and an appetite enhancing server 130, which may all be interconnected via a network 108. While programming and data of the exemplary embodiments may be stored and accessed remotely across several servers via the network 108, programming and data of the exemplary embodiments may alternatively or additionally be stored locally on as few as one physical computing device or amongst other computing devices than those depicted.

In the exemplary embodiments, the network 108 may be a communication channel capable of transferring data between connected devices. Accordingly, the components of the appetite enhancing system 100 may represent network components or network devices interconnected via the network 108. In the exemplary embodiments, the network 108 may be the Internet, representing a worldwide collection of networks and gateways to support communications between devices connected to the Internet. Moreover, the network 108 may utilize various types of connections such as wired, wireless, fiber optic, etc. which may be implemented as an intranet network, a local area network (LAN), a wide area network (WAN), or a combination thereof. In further embodiments, the network 108 may be a Bluetooth network, a Wi-Fi network, or a combination thereof. In yet further embodiments, the network 108 may be a telecommunications network used to facilitate telephone calls between two or more parties comprising a landline network, a wireless network, a closed network, a satellite network, or a combination thereof. In general, the network 108 may represent any combination of connections and protocols that will support communications between connected devices.

In the exemplary embodiments, the AR device 110 may be a wearable device capable of overlaying/superimposing computer-generated images upon a user's view of a real-world scene. In embodiments, the AR device 110 may include one or more sensors 112, and may be an enterprise server, a laptop computer, a notebook, a tablet computer, a netbook computer, a personal computer (PC), a desktop computer, a server, a personal digital assistant (PDA), a rotary phone, a touchtone phone, a smart phone, a mobile phone, a virtual device, a thin client, an IoT device, or any other electronic device or computing system capable of receiving and sending data to and from other computing devices. While the AR device 110 is shown as a single device, in other embodiments, the AR device 110 may be comprised of a cluster or plurality of computing devices, in a modular manner, etc., working together or working independently. The AR device 110 is described in greater detail as a hardware implementation with reference to FIG. 4, as part of a cloud implementation with reference to FIG. 5, and/or as utilizing functional abstraction layers for processing with reference to FIG. 6.

In example embodiments, the sensors 112 may comprise a camera, microphone, light sensor, infrared sensor, movement detection sensor, olfactory sensor, thermometer, pressure detection sensor, speedometer, accelerometer, gyroscope, global positioning system (GPS) sensor, or other sensory hardware equipment. Moreover, the AR device 110 may incorporate an array of the one or more sensors 112 such that information can be obtained by the sensors 112 in multiple directions, at different times/intervals, in different mediums/frequencies, and the like. For example, the AR device 110 may be a pair of goggles that includes three forward-facing cameras that each record an adjacent sixty-degree viewing angle spanning a total of one-hundred and eighty degrees in front of a user. Moreover, data processing techniques may be implemented such that directional information of visual and audio data can be obtained based on signals received by each of the three sensors 112, such as trilateration and triangulation.

While the sensors 112 are depicted as integrated with the AR device 110, in embodiments, the sensors 112 may be incorporated within an environment in which the appetite enhancing system 100 is implemented. For example, the sensors 112 may be one or more microphones built into an auditorium, a camera built into a facility, etc. Moreover, data processing techniques may be implemented such that directional information of visual and audio data can be obtained based on signals received by each of the sensors 112, such as trilateration and triangulation. In other embodiments, the sensors 112 may be integrated with other smart devices, e.g., smart phones and laptops, within an environment implementing the appetite enhancing system 100. In such embodiments, the sensors 112 may communicate directly with other networks and devices, such as the network 108. The sensors 112 are described in greater detail as a hardware implementation with reference to FIG. 4, as part of a cloud implementation with reference to FIG. 5, and/or as utilizing functional abstraction layers for processing with reference to FIG. 6.

In the example embodiment, the smart device(s) 120 include an appetite enhancing client 122, and may be an enterprise server, a laptop computer, a notebook, a tablet computer, a netbook computer, a personal computer (PC), a desktop computer, a server, a personal digital assistant (PDA), a rotary phone, a touchtone phone, a smart phone, a mobile phone, a virtual device, a thin client, an IoT device, or any other electronic device or computing system capable of receiving and sending data to and from other computing devices. While each smart device 120 is shown as a single device, in other embodiments, each smart device 120 may be comprised of a cluster or plurality of computing devices, in a modular manner, etc., working together or working independently. The smart device 120 is described in greater detail as a hardware implementation with reference to FIG. 4, as part of a cloud implementation with reference to FIG. 5, and/or as utilizing functional abstraction layers for processing with reference to FIG. 6.

The appetite enhancing client 122 may act as a client in a client-server relationship. The appetite enhancing client 122 may also be a software and/or hardware application capable of communicating with and providing a user interface for a user to interact with a server, for example the appetite enhancing server 130, via the network 108. Moreover, in the example embodiment, the appetite enhancing client 122 may be capable of transferring data from the AR device 110 and/or the sensors 112 between one or more smart devices 120 and other devices via the network 108. In embodiments, the appetite enhancing client 122 utilizes various wired and wireless connection protocols for data transmission and exchange, including Bluetooth, 2.4gHz and 5gHz internet, near-field communication, Z-Wave, Zigbee, etc. The appetite enhancing client 122 is described in greater detail with respect to FIG. 2.

In the exemplary embodiments, the appetite enhancing server 130 may include one or more appetite enhancing models 132 and an appetite enhancer 134, and may act as a server in a client-server relationship with the appetite enhancing client 122. The appetite enhancing server 130 may be an enterprise server, a laptop computer, a notebook, a tablet computer, a netbook computer, a PC, a desktop computer, a server, a PDA, a rotary phone, a touchtone phone, a smart phone, a mobile phone, a virtual device, a thin client, an IoT device, or any other electronic device or computing system capable of receiving and sending data to and from other computing devices. While the appetite enhancing server 130 is shown as a single device, in other embodiments, the appetite enhancing server 130 may be comprised of a cluster or plurality of computing devices, working together or working independently. The appetite enhancing server 130 is described in greater detail as a hardware implementation with reference to FIG. 4, as part of a cloud implementation with reference to FIG. 5, and/or as utilizing functional abstraction layers for processing with reference to FIG. 6.

The appetite enhancing models 132 may be one or more algorithms modelling a correlation between one or more features and one or more appetite enhancements for a user. In the example embodiment, the appetite enhancing models 132 may be generated using machine learning methods, such as neural networks, deep learning, hierarchical learning, Gaussian Mixture modelling, Hidden Markov modelling, and K-Means, K-Medoids, or Fuzzy C-Means learning, etc., and may model a likelihood of the one or more features being indicative of one or more appetite enhancements for a user, such as visual (enhance color, shape, quantity, type, etc. of consumable item), audio (enhance comforting sounds or music, muffle or mute annoying sounds), and/or olfactory (emitting comforting and/or appetizing smells) enhancements. In embodiments, such features may relate to consumable items and include colors, shapes, textures, ingredients, smells, temperatures, sizes, amounts, etc. Such features may additionally relate to a user's environment and include smells, sounds, lighting, temperature, cleanliness, movement, etc. The appetite enhancing models 132 may weight the features based on an effect that the features have on determining one or more appropriate appetite enhancements for a user.

In the exemplary embodiments, the appetite enhancer 134 may be a software and/or hardware program capable of collecting training data, extracting features from the training data, and training one or more models based on the extracted features. The appetite enhancer 134 may additionally be capable of configuring a session and detecting a user interacting with one or more consumable items (i.e., food, drink, paste, etc.). The appetite enhancer 134 may be further configured for collecting data of the one or more consumable items, extracting features from the collected data, and applying one or more models to the extracted features to determine one or more appropriate appetite enhancements for the user. Moreover, the appetite enhancer 134 may be further configured for notifying the user of the determined one or more appropriate appetite enhancements and enhancing the user's appetite. The appetite enhancer 134 is additionally capable of evaluating whether the user's appetite was appropriately enhanced and adjusting the one or more models. The appetite enhancer 134 is described in greater detail with reference to FIG. 2.

Figure 2:
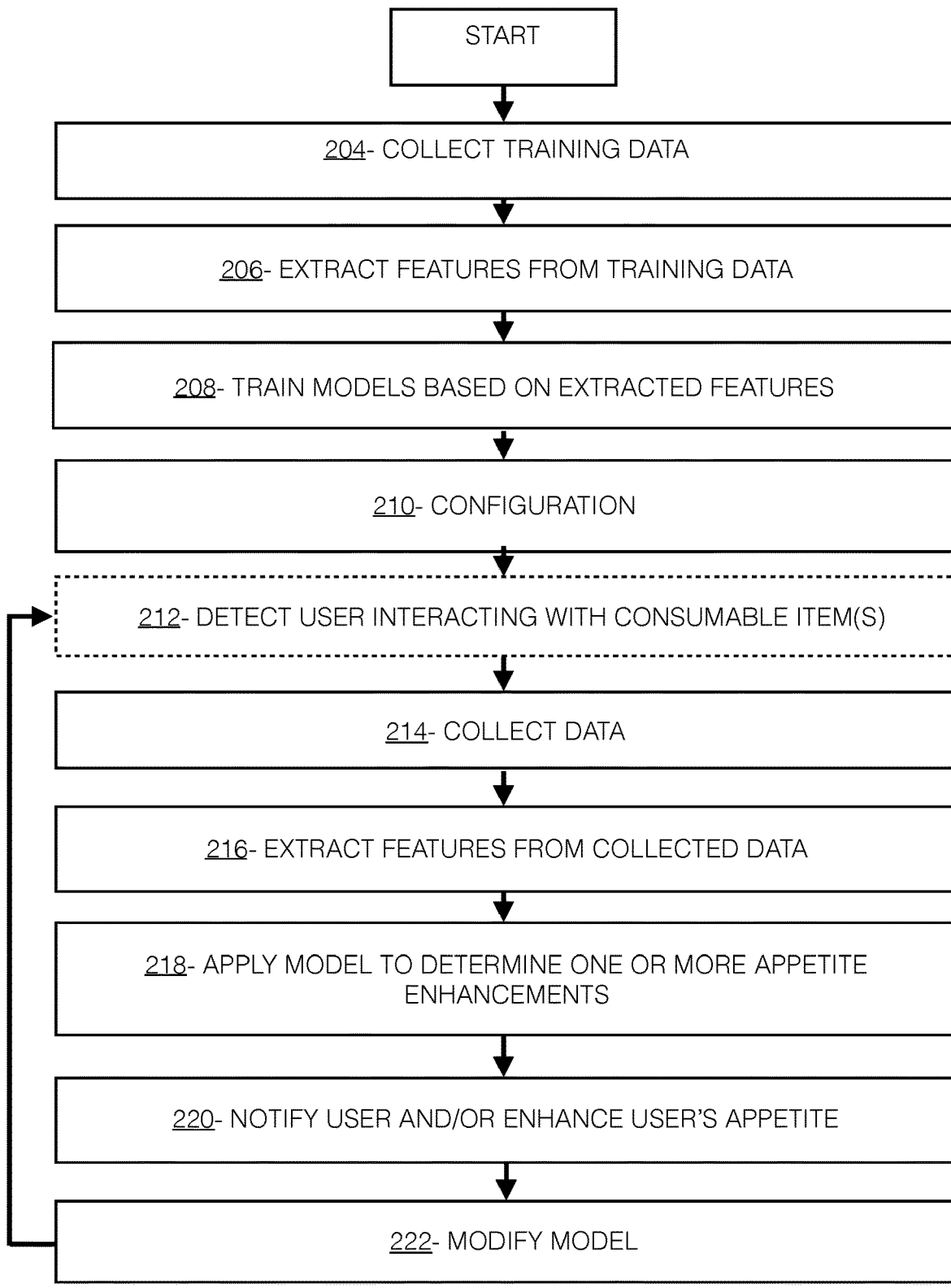
FIG. 2 depicts an exemplary flowchart illustrating the operations of an appetite enhancer 134 of the appetite enhancing system 100 in enhancing a user's appetite, in accordance with the exemplary embodiments.

FIG. 2 depicts an exemplary flowchart illustrating the operations of an appetite enhancer 134 of the appetite enhancing system 100 in enhancing a user's appetite, in accordance with the exemplary embodiments. In exemplary embodiments, the appetite enhancer 134 first implements a training phase in which it trains the appetite enhancing models 132 using labelled training data from previous user interactions with consumable items. The appetite enhancer 134 then moves on to an operational phase in which it applies the trained appetite enhancing models 132 to one or more current users consuming one or more consumable items to determine one or more appropriate appetite enhancements for the one or more users.

The appetite enhancer 134 may collect and/or receive training data (step 204). In embodiments, the training data may be sourced from one or more previous user interactions with consumable items. Training data may include data of one or more users consuming one or more items labelled with one or more enjoyment scores. For example, training data may include audio, video, olfactory, etc. data from one or more sensors 112 and databases of a user eating fish at a restaurant labelled with a high enjoyment score. In another example, training data may include audio, video, olfactory, etc. data from one or more sensors 112 and databases of a user eating fast food at a crowded and noisy food court labelled with a low enjoyment score. In embodiments, collected training data may be labelled such that features of the training data are correlated with enjoyment scores. The appetite enhancer 134 may retrieve training data via user upload, databases, or the sensors 112. The appetite enhancer 134 may collect training data from microphones, video cameras, and olfactory sensors built into the user's AR device 110. In embodiments, the appetite enhancer 134 may collect training data via the sensors 112 as one or more microphones built into an auditorium, a camera built into a facility, etc. The collected training data may be related to one or more consumable items and include colors, shapes, textures, ingredients, smells, temperatures, sizes, amounts, etc. and/or may be related to a user's environment and include smells, sounds, lighting, temperature, cleanliness, movement, etc.

To further illustrate the operations of the appetite enhancer 134, reference is now made to an illustrative example where the appetite enhancer 134 collects training data of various users eating various consumable items labelled with corresponding enjoyment scores.

The appetite enhancer 134 may extract one or more features from the collected and/or received training data (step 206). The extracted features may be extracted from the audio, video, olfactory, etc. data and/or databases, and may include features related to one or more consumable items such as colors, shapes, textures, ingredients, smells, temperatures, sizes, amounts, etc. The extracted features may additionally relate to a user's environment and include smells, sounds, lighting, temperature, cleanliness, movement (i.e., walking, sitting in a moving vehicle, etc.), etc. In embodiments, the appetite enhancer 134 may use techniques such as feature extraction, natural language processing, named entity recognition, optical character recognition, image processing, audio processing, olfactory processing, pattern/template matching, data comparison, convolutional neural networks, cosine similarity, binary classifiers, etc. to identify features. For example, if video data of a user eating broccoli is collected, the appetite enhancer 134 may use image processing, video processing, and feature extraction to extract colors, shapes, textures, sizes, amounts, etc. of the broccoli as well as lighting, cleanliness, and movement of the user's surrounding environment. If audio data of a user saying, "This is way too much broccoli" or "This broccoli doesn't look very fresh" is collected, the appetite enhancer 134 may use audio processing and natural language processing to extract color, texture, sizes, and amounts of the broccoli, in addition to sounds of crowdedness extracted from background noise. The appetite enhancer 134 may further extract smells from collected olfactory data via olfactory processing techniques, temperatures from thermometers via feature extraction, and ingredients from databases via object character recognition. The appetite enhancer 134 may later associate extracted features with one or more appropriate appetite enhancements for a user when training one or more models.

With reference to the previously introduced example where the appetite enhancer 134 collects training data of various users eating various consumable items labelled with corresponding enjoyment scores, the appetite enhancer 134 extracts consumable item features such as colors, shapes, textures, ingredients, smells, temperatures, sizes, amounts, etc. as well as environment features such as smells, sounds, lighting, temperature, cleanliness, movement, etc. from the collected training data.

The appetite enhancer 134 may train one or more appetite enhancing models 132 based on the extracted features (step 208). The appetite enhancer 134 may train one or more appetite enhancing models 132 based on an association of the one or more extracted features with one or more appetite enhancements for a user. As previously mentioned, such extracted features may include features related to one or more consumable items such as colors, shapes, textures, ingredients, smells, temperatures, sizes, amounts, etc. The extracted features may additionally relate to a user's environment and include smells, sounds, lighting, temperature, cleanliness, movement, etc., and the one or more appetite enhancing models 132 may be generated through machine learning techniques such as neural networks, cosine similarity, binary classifier, etc. Moreover, the appetite enhancer 134 may train the one or more appetite enhancing models 132 to weight the features such that features shown to have a greater correlation with determining one or more appropriate appetite enhancements for a user are weighted greater than those features that are not. In embodiments, the appetite enhancing models 132 may include a model for each user. In other embodiments, the appetite enhancer 134 may simply train one appetite enhancing model 132 to be later applied to all users. In embodiments, the appetite enhancer 134 may train one or more appetite enhancing models 132 based on one or more you only look once algorithm, to learn image sources relevant to consumable items and apply hierarchical clustering to bucket them into different categories. Based on the appetite enhancing models 132's extracted features and weights associated with such extracted features, the appetite enhancer 134 may later determine one or more appropriate appetite enhancements for a user.

With reference to the previously introduced example where the appetite enhancer 134 extracts consumable item features such as colors, shapes, textures, ingredients, smells, temperatures, sizes, amounts, etc. as well as environment features such as smells, sounds, lighting, temperature, cleanliness, movement, etc. from the collected training data, the appetite enhancer 134 trains a model for each user of the collected training data.

The appetite enhancer 134 may receive a configuration (step 210). Having trained the one or more appetite enhancing models 132, the appetite enhancer 134 may now apply the one or more appetite enhancing models 132 to one or more users' interactions with consumable items in real time. The appetite enhancer 134 may first, however, receive a user configuration by receiving a user registration and user preferences. The user registration may be uploaded by a user, i.e., a person wearing the AR device 110 or person responsible for the wearer of the AR device 110 of the appetite enhancing system 100 (i.e., parent of a child, caretaker for an elderly person, etc.), and the configuration may be received by the appetite enhancer 134 via the appetite enhancing client 122 and the network 108. Receiving the user registration may involve referencing a user profile via user login credentials, internet protocol (IP) address, media access control (MAC) address, etc., or receiving user input information such as a name, date of birth, gender, address/geographic information, phone number, email address, company name, device serial numbers, one or more smart device 120 types, AR device 110 type, sensors 112 types, and the like. Receiving a user registration may also involve receiving or extracting data from databases or the internet via network 108 (i.e., from internet searches, social media accounts, etc.) such as allergy information, medical history, favorite and least favorite consumable item preferences, environment preferences, etc. of a user. Lastly, the appetite enhancer 134 may receive a configuration of the one or more sensors 112, whether they be fixed to one or more devices (e.g., the one or more smart devices 120 or the AR device 110) or fixed within an environment in which the appetite enhancing system 100 is implemented.

During configuration, the appetite enhancer 134 may further receive user preferences (step 210 continued). User preferences may include preferences for the manner in which the appetite enhancer 134 should enhance a user's appetite. For example, user preferences may specify notifying the user and/or the user's caregiver, parent, child, etc. and waiting for feedback or confirmation from the user, caregiver, parent, child, etc. before enhancing the user's appetite. For example, a user may upload user preferences specifying that the user's caregiver must confirm determined appetite enhancements prior to the appetite enhancer 134 enhancing the user's appetite. In another example, a user may upload user preferences specifying that the appetite enhancer 134 is to enhance the user's appetite upon determination of one or more appropriate appetite enhancements for the user.

With reference to the previously introduced example where the appetite enhancer 134 trains a model for each user of the collected training data, the appetite enhancer 134 receives a user registration via user upload including the user's name, user's caregiver's name, allergy information, medical history information, type of smart device 120, type of AR device 110, type of sensors 112 including a microphone, video camera, and olfactory sensor located on the AR device 110. The appetite enhancer 134 also receives user preferences via user upload specifying that the appetite enhancer 134 is to immediately enhance the user's appetite upon determining one or more suitable appetite enhancements.

The appetite enhancer 134 may optionally detect the user interacting with one or more consumable items (optional step 212). In embodiments, the appetite enhancer 134 may detect the user interacting with one or more consumable items by identifying one or more consumable items near a user from video data or olfactory data collected by the sensors 112 (i.e., via image processing, video processing, feature extraction, cosine similarity, binary classifier, etc.) For example, if a user uses a fork to interact with a plate of food, the appetite enhancer 134 may detect the user interacting with one or more consumable items. In embodiments, the appetite enhancer 134 may detect the user interacting with one or more consumable items via a toggle switch, button, slider, etc. that may be selected by the user manually by hand using a button/touchscreen/etc., by voice, by eye movement, and the like. In embodiments, the appetite enhancer 134 may not detect the user interacting with one or more consumable items, but rather continuously collect data of the user and the user's surroundings.

With reference to the previously introduced example where the appetite enhancer 134 receives a user registration and user preferences, the appetite enhancer 134 detects the user interacting with a plate of spinach via the video camera sensor 112.

Upon detecting the user interacting with one or more consumable items, the appetite enhancer 134 may collect data of the one or more consumable items and the user's surroundings (step 214). In embodiments, the appetite enhancer 134 may begin collecting data when receiving a trigger from the user. As previously discussed, the appetite enhancer 134 may be triggered via a toggle switch, button, slider, etc. that may be selected by the user manually by hand using a button/touchscreen/etc., by voice (trigger word, trigger phrase), by eye movement, etc. Alternatively, the appetite enhancer 134 may continuously collect data of a user in anticipation of the user interacting with one or more consumable items. Anticipation may be based on user movement, for example detected by one or more sensors 112. Anticipation may be based on the user entering a geofence or connecting to network 108. The appetite enhancer 134 may retrieve data of the one or more consumable items and the user's surroundings via the sensors 112, which may include one or more microphones built into an auditorium, a camera built into a facility, etc. The appetite enhancer 134 may additionally retrieve data of the user's consumable item and environment preferences such as allergies, medical history, favorite and least favorite consumable item preferences, favorite eating environments or ambiances, etc. from one or more databases or the internet (i.e., via internet searches, social media accounts, etc.) accessed via network 108. The collected data may be related to consumable items and include colors, shapes, textures, ingredients, smells, temperatures, sizes, amounts, etc. The collected data may additionally relate to a user's environment and include smells, sounds, lighting, temperature, cleanliness, movement, etc.

With reference to the previously introduced example where the appetite enhancer 134 detects the user interacting with a plate of spinach via the video camera sensor 112, the appetite enhancer 134 collects video data, audio data, and olfactory data from the video camera, microphone, and olfactory sensors 112. The appetite enhancer 134 additionally collects data of the user's consumable item and environment preferences from the databases received during configuration.

The appetite enhancer 134 may extract one or more features from the collected and/or received data (step 216). The appetite enhancer 134 may extract one or more features from the collected and/or received data in the same manner as described with reference to step 206, however here the features are extracted not from the training data, but rather from the data of the current user and one or more consumable items.

With reference to the previously introduced example where the appetite enhancer 134 collects data, the appetite enhancer 134 extracts spinach features: green but mild discoloring, slimy texture, bitter spinach smell, warm temperature, large quantity. The appetite enhancer 134 additionally extracts environment features: pungent gasoline smell, bright lighting, loud machinery noise, walking.

The appetite enhancer 134 may apply one or more models to the extracted features to determine one or more appropriate appetite enhancements for the user (step 218). As previously mentioned, such extracted features may relate to consumable items and include colors, shapes, textures, ingredients, smells, temperatures, sizes, amounts, etc. The extracted features may additionally relate to a user's environment and include smells, sounds, lighting, temperature, cleanliness, movement, etc., and the one or more appetite enhancing models 132 may be generated through machine learning techniques such as neural networks. In embodiments, the one or more appetite enhancing models 132 may be trained at initialization and/or through the use of a feedback loop to weight the features such that features shown to have a greater correlation with determining one or more appropriate appetite enhancements for a user are weighted greater than those features that are not. Based on the extracted features and weights associated with such extracted features, the appetite enhancer 134 may determine one or more appropriate appetite enhancements for a user. For example, if a user is eating a type of food that they dislike in a noisy food court, the appetite enhancer 134 may determine that olfactory, visual, and audio augmented reality effects such as emitting a smell of the user's favorite food, enhancing the color and texture of the disliked food, and muffling the noisy surrounding sounds are appropriate to enhance the user's appetite. In another example, if a child is eating a vegetable that they dislike, the appetite enhancer 134 may determine that displaying images of colorful toys near the vegetable and emitting cartoon sound effects may enhance the child's appetite.

With reference to the previously introduced example where the appetite enhancer 134 extracts spinach features: green but mild discoloring, slimy texture, bitter spinach smell, warm temperature, large quantity and environment features: pungent gasoline smell, bright lighting, loud machinery noise, the appetite enhancer 134 applies a model to determine that color, texture, and movement smoothing visual enhancements, fresh bread olfactory enhancements, and calming music audio enhancements and background sound muffling would enhance the user's appetite for the spinach.

Upon the appetite enhancer 134 determining one or more appropriate appetite enhancements for a user, the appetite enhancer 134 may notify one or more users and/or enhance the user's appetite (step 220). In embodiments, the appetite enhancer 134 may notify the user (and/or user's caretakers, parents, children, etc.) of one or more enhancements and wait for confirmation from the user before enhancing the user's appetite according to user preferences. The appetite enhancer 134 may notify one or more users by audio, video, text, or any other manner via the AR device 110 and/or the smart device 120. The appetite enhancer 134 may enhance the user's appetite by displaying one or more images or image modifications via overlay within a display of the AR device 110 (i.e., familiar items for a user with dementia, displaying toys for a child, etc.), emitting one or more smells via the AR device 110 (i.e., familiar smells for a user with dementia, the smell of chocolate for a child, etc.), emitting (i.e., classical music, user's preferred music, etc.) or muffling (i.e., cancelling out) one or more sounds via headphones or speakers attached to the AR device 110 or smart device 120, etc. For example, the appetite enhancer 134 may overlay a three-dimensional image of a user's favorite food item next to or on the food item they are current consuming, play calming music, remove distracting objects from the user's field of view, and emit the smell of fresh bread. As discussed with reference to configuration, the appetite enhancer 134 may notify the user of one or more appetite enhancements according to the user preferences of configuration. In embodiments, the appetite enhancer 134 may be configured for receiving user input acknowledging, dismissing, and/or affirming that the one or more enhancements are appropriate and should be implemented.

With reference to the previously introduced example where the appetite enhancer 134 applies a model to determine that color, texture, and movement smoothing visual enhancements, fresh bread olfactory enhancements, and calming music audio enhancements and background sound muffling would enhance the user's appetite for the spinach, the appetite enhancer 134 immediately enhances the user's appetite according to user preferences.

The appetite enhancer 134 may evaluate and modify the appetite enhancing models 132 (step 222). In the example embodiment, the appetite enhancer 134 may verify whether the one or more appetite enhancements were appropriate or helped enhance the user's appetite in order to provide a feedback loop for modifying the appetite enhancing models 132. In embodiments, the feedback loop may simply provide a means for the user to indicate whether the one or more consumable items tasted better than anticipated. The feedback loop indication may be triggered via a toggle switch, button, slider, etc. that may be selected by the user manually by hand using a button/touchscreen/etc., by voice, by eye movement, and the like. Based on the appetite enhancer 134 appropriately or inappropriately enhancing the user's appetite, the appetite enhancer 134 may modify the appetite enhancing models 132. In other embodiments, the appetite enhancer 134 may infer or deduce whether the user's appetite was enhanced. For example, the appetite enhancer 134 may interpret user dialogue via natural language processing to determine whether the user's appetite was enhanced. For example, if the user says, "Oh, not as bad as I thought" or other expressions indicative of a user's surprise or satisfaction, the appetite enhancer 134 may infer that the user's appetite was enhanced and modify the appetite enhancing models 132 accordingly. In another example, if the user consumes the consumable items quickly or without delay, the appetite enhancer 134 may determine that the user's appetite was enhanced. In another example, a user's facial expression may be tracked while the user consumes items and scored on a scale of 1-5 (1 being dissatisfied, 5 being satisfied). The appetite enhancer 134 may further enhance the user's appetite upon detecting the user's facial expression indicating dissatisfaction (i.e., further enhance if user's satisfaction score is less than 3). Based on feedback received in the above or any other manners, the appetite enhancer 134 may then modify the appetite enhancing models 132 to more accurately enhance a user's appetite.

With reference to the previously introduced example where the appetite enhancer 134 enhances the user's appetite according to user preferences, the user says, "This spinach isn't nearly as bad as I thought" and the appetite enhancer 134 modifies the appetite enhancing models 132 accordingly.

Figure 3:
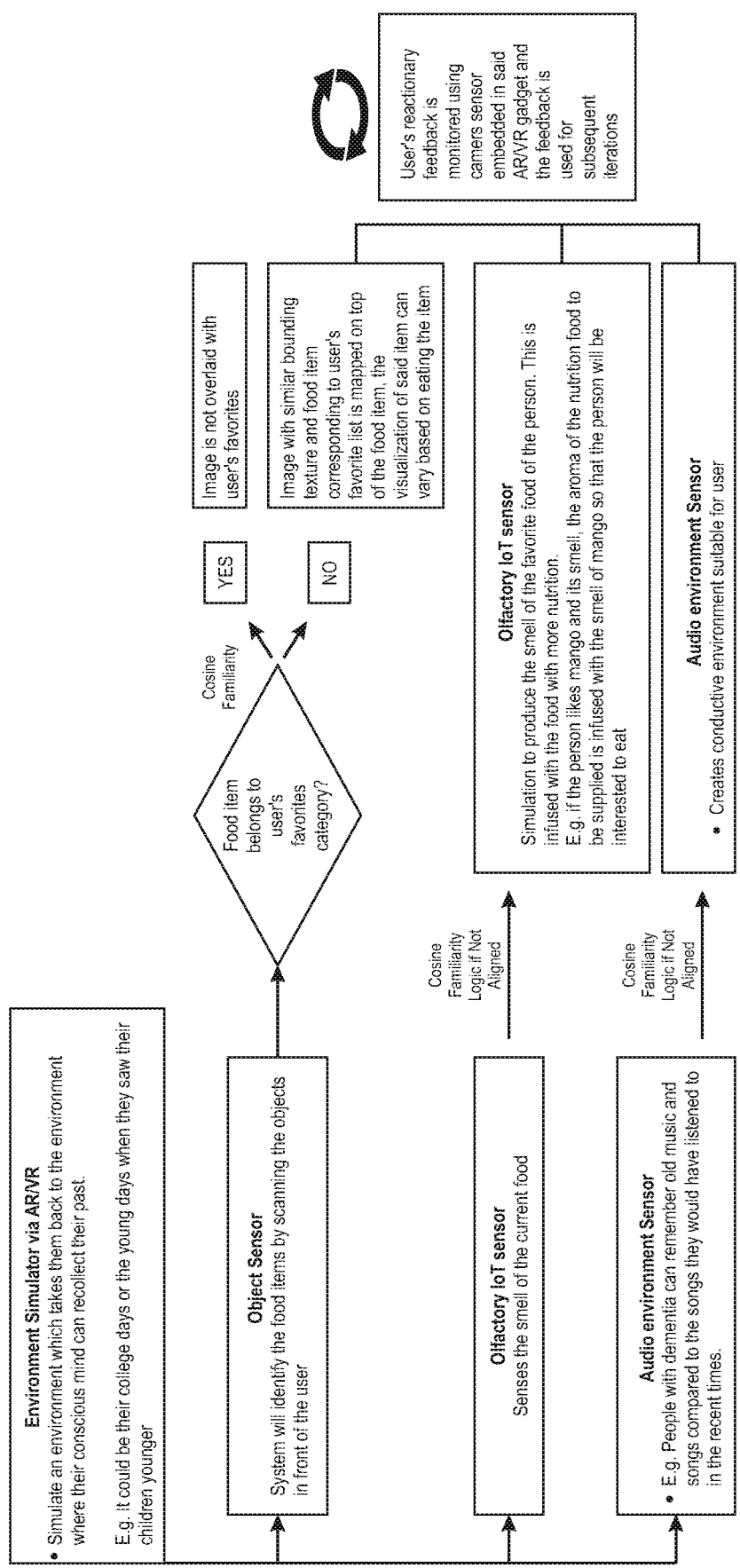
FIG. 3 depicts an exemplary flowchart illustrating the operations of an appetite enhancer 134 of the appetite enhancing system 100 in enhancing a user's appetite, in accordance with the exemplary embodiments.

FIG. 3 depicts an exemplary flowchart illustrating the operations of an appetite enhancer 134 of the appetite enhancing system 100 in enhancing a user's appetite, in accordance with the exemplary embodiments.

Figure 4:
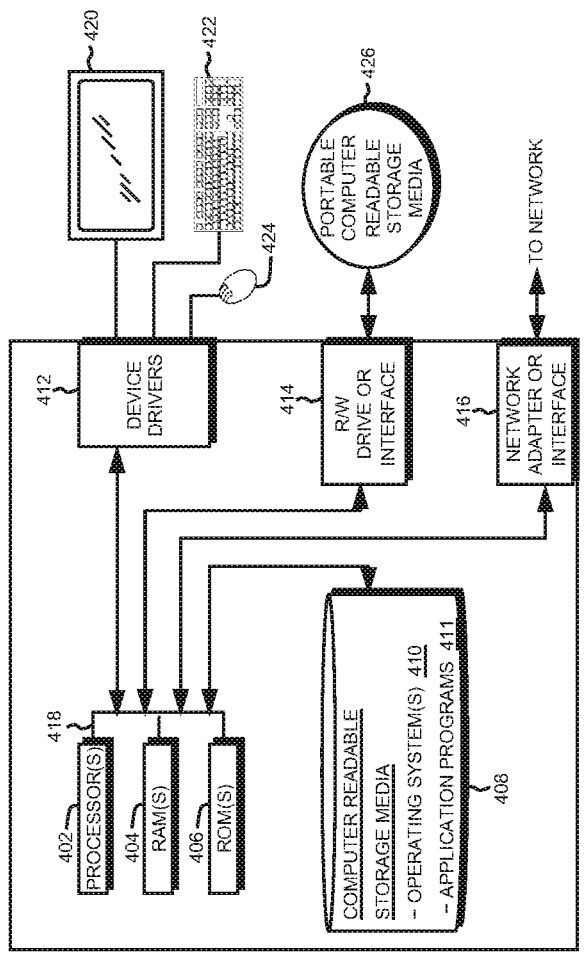
FIG. 4 depicts an exemplary block diagram depicting the hardware components of the appetite enhancing system 100 of FIG. 1, in accordance with the exemplary embodiments.

FIG. 4 depicts a block diagram of devices within the appetite enhancing system 100 of FIG. 1, in accordance with the exemplary embodiments. It should be appreciated that FIG. 4 provides only an illustration of one implementation and does not imply any limitations with regard to the environments in which different embodiments may be implemented. Many modifications to the depicted environment may be made.

Devices used herein may include one or more processors 402, one or more computer-readable RAMs 404, one or more computer-readable ROMs 406, one or more computer readable storage media 408, device drivers 412, read/write drive or interface 414, network adapter or interface 416, all interconnected over a communications fabric 418. Communications fabric 418 may be implemented with any architecture designed for passing data and/or control information between processors (such as microprocessors, communications and network processors, etc.), system memory, peripheral devices, and any other hardware components within a system.

One or more operating systems 410, and one or more application programs 911 are stored on one or more of the computer readable storage media 408 for execution by one or more of the processors 402 via one or more of the respective RAMs 404 (which typically include cache memory). In the illustrated embodiment, each of the computer readable storage media 08 may be a magnetic disk storage device of an internal hard drive, CD-ROM, DVD, memory stick, magnetic tape, magnetic disk, optical disk, a semiconductor storage device such as RAM, ROM, EPROM, flash memory or any other computer-readable tangible storage device that can store a computer program and digital information.

Devices used herein may also include a R/W drive or interface 414 to read from and write to one or more portable computer readable storage media 426. Application programs 411 on said devices may be stored on one or more of the portable computer readable storage media 408, read via the respective RAY drive or interface 414 and loaded into the respective computer readable storage media 408.

Devices used herein may also include a network adapter or interface 416, such as a TCP/IP adapter card or wireless communication adapter (such as a 4G wireless communication adapter using OFDMA technology). Application programs 411 on said computing devices may be downloaded to the computing device from an external computer or external storage device via a network (for example, the Internet, a local area network or other wide area network or wireless network) and network adapter or interface 416. From the network adapter or interface 416, the programs may be loaded onto computer readable storage media 408. The network may comprise copper wires, optical fibers, wireless transmission, routers, firewalls, switches, gateway computers and/or edge servers.

Devices used herein may also include a display screen 420, a keyboard or keypad 422, and a computer mouse or touchpad 424. Device drivers 412 interface to display screen 420 for imaging, to keyboard or keypad 422, to computer mouse or touchpad 424, and/or to display screen 420 for pressure sensing of alphanumeric character entry and user selections. The device drivers 412, RAY drive or interface 414 and network adapter or interface 416 may comprise hardware and software (stored on computer readable storage media 408 and/or ROM 406).

The programs described herein are identified based upon the application for which they are implemented in a specific one of the exemplary embodiments. However, it should be appreciated that any particular program nomenclature herein is used merely for convenience, and thus the exemplary embodiments should not be limited to use solely in any specific application identified and/or implied by such nomenclature.

Based on the foregoing, a computer system, method, and computer program product have been disclosed. However, numerous modifications and substitutions can be made without deviating from the scope of the exemplary embodiments. Therefore, the exemplary embodiments have been disclosed by way of example and not limitation.

It is to be understood that although this disclosure includes a detailed description on cloud computing, implementation of the teachings recited herein are not limited to a cloud computing environment. Rather, the exemplary embodiments are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or data center).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure that includes a network of interconnected nodes.

Figure 5:
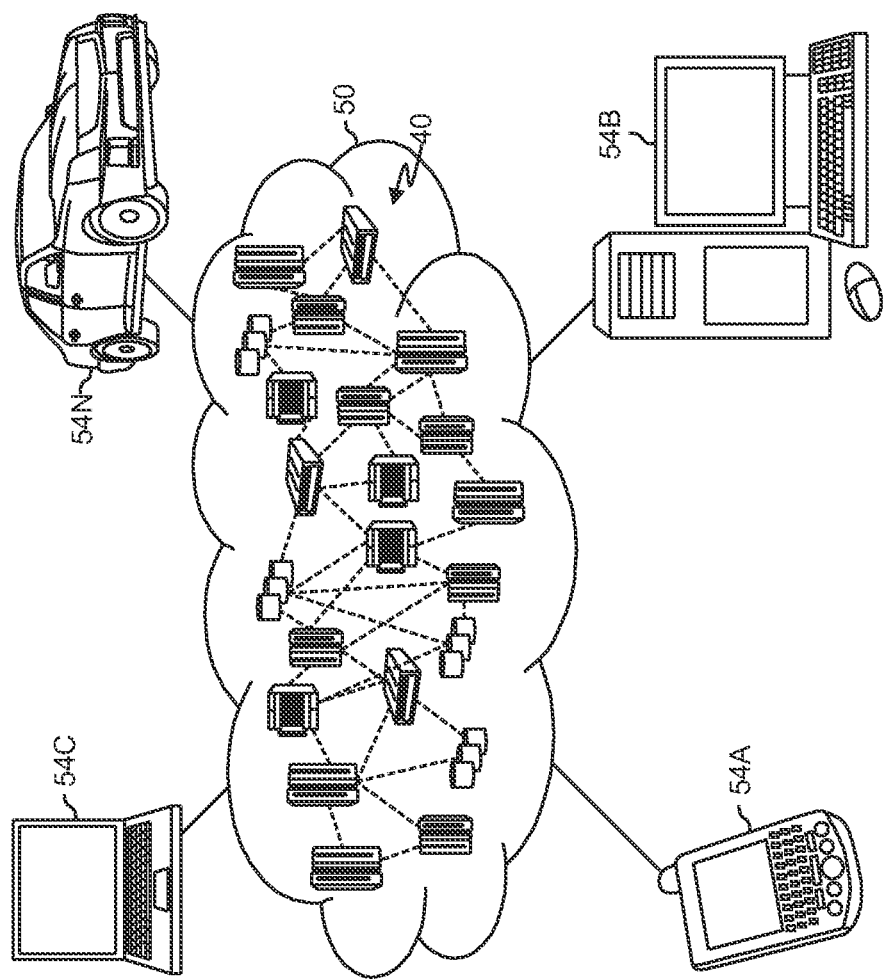
FIG. 5 depicts a cloud computing environment, in accordance with the exemplary embodiments.

Referring now to FIG. 5, illustrative cloud computing environment 50 is depicted. As shown, cloud computing environment 50 includes one or more cloud computing nodes 40 with which local computing devices used by cloud consumers, such as, for example, personal digital assistant (PDA) or cellular telephone 54A, desktop computer 54B, laptop computer 54C, and/or automobile computer system 54N may communicate. Nodes 40 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 5 are intended to be illustrative only and that computing nodes 40 and cloud computing environment 50 can communicate with any type of computerized device over any type of network and/or network addressable connection (e.g., using a web browser).

Figure 6:
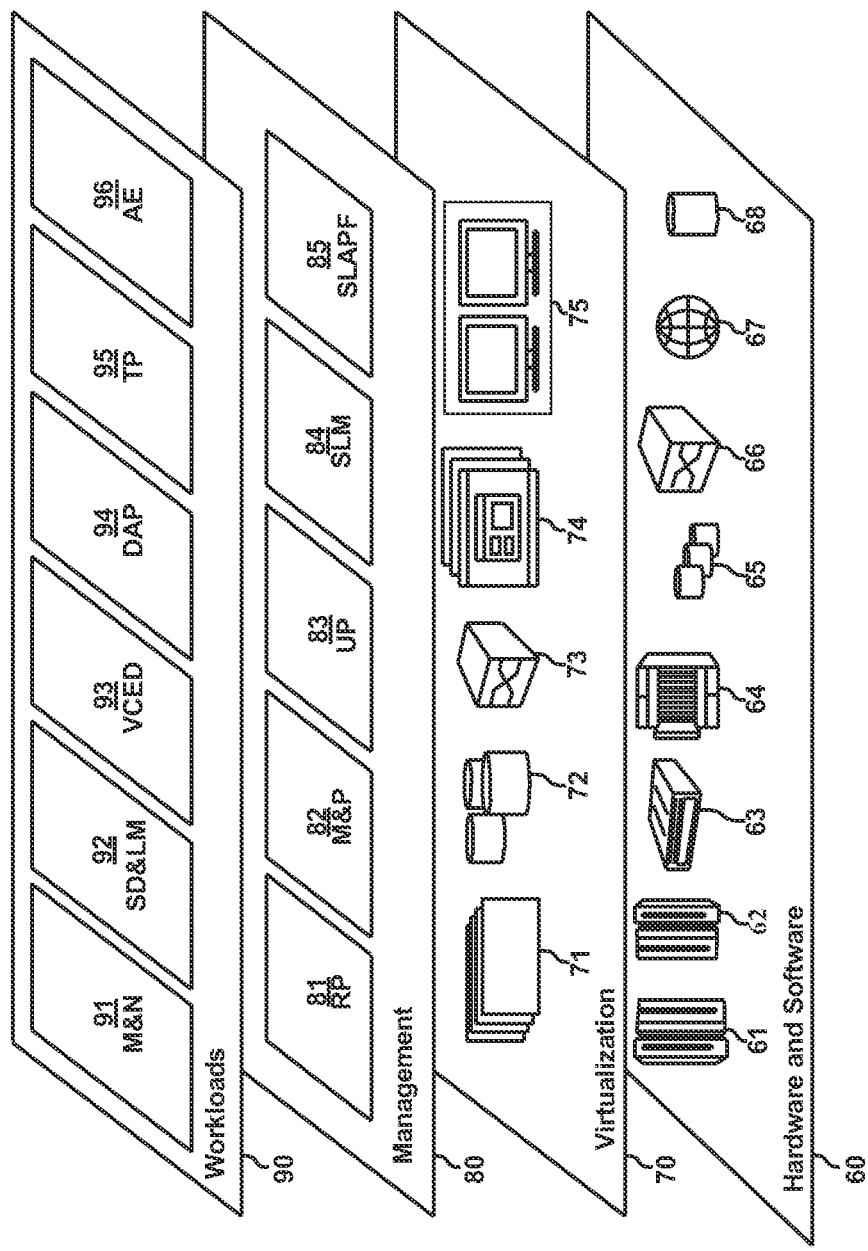
FIG. 6 depicts abstraction model layers, in accordance with the exemplary embodiments.

Referring now to FIG. 6, a set of functional abstraction layers provided by cloud computing environment 50 (FIG. 5) is shown. It should be understood in advance that the components, layers, and functions shown in FIG. 6 are intended to be illustrative only and the exemplary embodiments are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and appetite enhancement 96.

The exemplary embodiments may be a system, a method, and/or a computer program product at any possible technical detail level of integration. The computer program product may include a computer readable storage medium (or media) having computer readable program instructions thereon for causing a processor to carry out aspects of the exemplary embodiments.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the exemplary embodiments may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the exemplary embodiments.

Aspects of the exemplary embodiments are described herein with reference to flowchart illustrations and/or block diagrams of methods, apparatus (systems), and computer program products according to the exemplary embodiments. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/ or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various exemplary embodiments. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

What is claimed is:

1. A computer-implemented method for enhancing a user's appetite with one or more augmented reality devices, the method comprising:
    collecting data of the user, the user's environment, and one or more consumable items;
    extracting one or more features from the collected data;
    determining one or more augmented reality appetite enhancements, via one or more appetite enhancing models, by training the one or more appetite enhancing models based on the extracted one or more features, the determining one or more augmented reality appetite enhancements including using training data sourced from one or more previous user interactions with the one or more consumable items to train the one or more appetite enhancing models;
    enhancing the user's appetite by way of the one or more augmented reality devices according to the determined one or more augmented reality appetite enhancements;
    receiving user feedback indicative of whether the one or more consumable items tasted better than anticipated;
    adjusting the one or more appetite enhancing models based on the received feedback; and
    determining, via natural language processing, whether the one or more augmented reality appetite enhancements enhanced the user's appetite.

2. The method of claim 1, wherein:
    enhancing the user's appetite comprises one or more visual, audio, or olfactory modifications to the user's augmented reality environment.

3. The method of claim 1, further comprising:
    notifying the user of the determined one or more augmented reality appetite enhancements prior to enhancing the user's appetite.

4. The method of claim 1, wherein the one or more appetite enhancing models correlate the one or more features with the likelihood of indicating one or more appropriate appetite enhancements for the user.

5. The method of claim 1, further comprising:
    collecting the training data, the training data including data of the user consuming one or more consumable items labeled with one or more enjoyment scores;
    extracting training features from the training data; and
    training one or more appetite enhancing models based on the extracted training features.

6. The method of claim 1, wherein:
    the one or more features include one or more features selected from the group consisting of consumable item colors, shapes, textures, ingredients, smells, temperatures, sizes, and amounts; and
    the one or more features include one or more features selected from the group consisting of environment smells, sounds, lighting, temperature, cleanliness, and movement.

7. A computer program product for enhancing a user's appetite with one or more augmented reality devices, the computer program product comprising:
    one or more non-transitory computer-readable storage media and program instructions stored on the one or more non-transitory computer-readable storage media capable of performing a method, the method comprising:
    collecting data of the user, the user's environment, and one or more consumable items;
    extracting one or more features from the collected data;
    determining one or more augmented reality appetite enhancements, via one or more appetite enhancing models, by training the one or more appetite enhancing models based on the extracted one or more features, the determining one or more augmented reality appetite enhancements including using training data sourced from one or more previous user interactions with the one or more consumable items to train the one or more appetite enhancing models;
    enhancing the user's appetite by way of the one or more augmented reality devices according to the determined one or more augmented reality appetite enhancements;
    receiving user feedback indicative of whether the one or more consumable items tasted better than anticipated;
    adjusting the one or more appetite enhancing models based on the received feedback; and
    determining, via natural language processing, whether the one or more augmented reality appetite enhancements enhanced the user's appetite.

8. The computer program product of claim 7, wherein:
    enhancing the user's appetite comprises one or more visual, audio, or olfactory modifications to the user's augmented reality environment.

9. The computer program product of claim 7, further comprising:
    notifying the user of the determined one or more augmented reality appetite enhancements prior to enhancing the user's appetite.

10. The computer program product of claim 7, wherein the one or more appetite enhancing models correlate the one or more features with the likelihood of indicating one or more appropriate appetite enhancements for the user.

11. The computer program product of claim 8, further comprising:
collecting the training data, the training data including data of the user consuming one or more consumable items labeled with one or more enjoyment scores;
extracting training features from the training data; and
training one or more appetite enhancing models based on the extracted training features.

12. The computer program product of claim 7, wherein:
the one or more features include one or more features selected from the group consisting of consumable item colors, shapes, textures, ingredients, smells, temperatures, sizes, and amounts; and
the one or more features include one or more features selected from the group consisting of environment smells, sounds, lighting, temperature, cleanliness, and movement.

13. A computer system for enhancing a user's appetite with one or more augmented reality devices, the computer system comprising:
one or more computer processors, one or more computer-readable storage media, and program instructions stored on the one or more of the computer-readable storage media for execution by at least one of the one or more processors capable of performing a method, the method comprising:
collecting data of the user, the user's environment, and one or more consumable items;
extracting one or more features from the collected data;
determining one or more augmented reality appetite enhancements, via one or more appetite enhancing models, by training the one or more appetite enhancing models based on the extracted one or more features, the determining one or more augmented reality appetite enhancements including using training data sourced from one or more previous user interactions with the one or more consumable items to train the one or more appetite enhancing models;
enhancing the user's appetite by way of the one or more augmented reality devices according to the determined one or more augmented reality appetite enhancements;
receiving user feedback indicative of whether the one or more consumable items tasted better than anticipated;
adjusting the one or more appetite enhancing models based on the received feedback; and
determining, via natural language processing, whether the one or more augmented reality appetite enhancements enhanced the user's appetite.

14. The computer system of claim 13, wherein:
enhancing the user's appetite comprises one or more visual, audio, or olfactory modifications to the user's augmented reality environment.

15. The computer system of claim 13, further comprising:
notifying the user of the determined one or more augmented reality appetite enhancements prior to enhancing the user's appetite.

16. The computer system of claim 13, wherein the one or more appetite enhancing models correlate the one or more features with the likelihood of indicating one or more appropriate appetite enhancements for the user.

17. The computer system of claim 13, further comprising:
collecting the training data, the training data including data of the user consuming one or more consumable items labeled with one or more enjoyment scores;
extracting training features from the training data; and
training one or more appetite enhancing models based on the extracted training features.

* * * * *